United States Patent
Asmussen et al.

(10) Patent No.: US 6,436,937 B1
(45) Date of Patent: Aug. 20, 2002

(54) USE OF DESOXYPEGANINE IN THE TREATMENT OF ALZHEIMER'S DEMENTIA

(75) Inventors: Bodo Asmussen, Bendorf; Thomas Hille; Hans-Rainer Hoffmann, both of Neuwied; Klaus Opitz, Münster, all of (DE)

(73) Assignee: LTS Lohman-Therapie Systeme AG, Andernach (DE)

( * ) Notice: Subject to any disclaimer, the term of this patent is extended or adjusted under 35 U.S.C. 154(b) by 0 days.

(21) Appl. No.: 09/913,638

(22) PCT Filed: Feb. 8, 2000

(86) PCT No.: PCT/EP00/00972

§ 371 (c)(1),
(2), (4) Date: Aug. 16, 2001

(87) PCT Pub. No.: WO00/48599

PCT Pub. Date: Aug. 24, 2000

(30) Foreign Application Priority Data

Feb. 19, 1999 (DE) .......................................... 199 06 975

(51) Int. Cl.[7] ...................... A61P 25/28; A61K 31/495; A61K 31/40; A61K 31/167; A61K 9/22

(52) U.S. Cl. ...................... 514/250; 514/523; 514/408; 514/349; 514/631; 514/906; 424/424; 424/422; 424/725; 424/776; 800/12

(58) Field of Search ................................. 514/250, 523, 514/408, 349, 631, 906; 424/422, 725, 776, 424; 800/12

(56) References Cited

U.S. PATENT DOCUMENTS 5,750,542 A    5/1998    Villalobos et al.

FOREIGN PATENT DOCUMENTS

WO    WO 97/23484    7/1997

OTHER PUBLICATIONS

Database WPI Section Ch, Week 197913 Derwent Publications Ltd., London, GB; Class B02, AN 1979–25213B (XP002139611).

Database WPI Section Ch, Week 198235 Derwent Publications Ltd., London, GB; Class B04, AN 1982–74317E (XP002139612).

Muratova, et al, "Toxicology of the new pharmaceutical preparation of dehydroxypeganine hydrochloride" Med. Zh. Uzb. 1984, (1), 53–5 (XP000957819) (abstract).

Heston et al, "Dementia of the Alzheimer Type" Arch. Gen. Psychiatry 1981, vol. 38 pp. 1085–1090.

Terry et al., "Senile Dementia of the Alzeimer Type: Defining A Disease" The Neurology of Aging, by Robert Katzman 1983, Ch.3, pp. 51–84.

Primary Examiner—Frederick Krass
Assistant Examiner—Clinton Ostrup
(74) Attorney, Agent, or Firm—Frommer Lawrence & Haug LLP

(57) ABSTRACT

The invention relates to a device and method for the treatment of Alzheimer's dementia with desoxypeganine and/or a pharmaceutically acceptable acid addition salt of desoxypeganine.

2 Claims, No Drawings

USE OF DESOXYPEGANINE IN THE TREATMENT OF ALZHEIMER'S DEMENTIA

The invention is directed at a device and a procedure for the treatment of Alzheimer's dementia with deoxypeganine and/or a pharmaceutically acceptable acid addition salt of deoxypeganine.

Alzheimer's dementia (Alzheimer's disease, senile dementia of the Alzheimer type, SDAT, AD, presenile dementia, senile dementia, primary degenerative dementia, PDD) is understood as meaning the clinical manifestation of a disturbance of the most highly developed areas of the brain. More precise descriptions can be gleaned, for example, in L. L. Heston et al., Arch. Gen. Psychiatry, (1981) 1085 or in R. Terry, R. Katzman: "Senile Dementia of the Alzheimer Type: Defining a Disease" in The Neurology of Aging, ed.: R. Katzman, Chapter 3, p. 51.

An exact diagnosis of Alzheimer's dementia is only possible post mortem by autopsy. For the person skilled in the art, however, it is possible on the basis of typical symptoms (increasing loss of intellectual capabilities and memory loss in the early stage; confusion, loss of the sense of orientation, abnormal sensory liability, depression, anxiety states, lack of motivation, disturbed social behavior, tiredness, weakened driving force, loss of weight etc. in the advanced stage) and in the absence of references to other causes to diagnose Alzheimer's dementia with high probability.

The cause of Alzheimer's dementia is still not known even today. Consequently no medicinal or other therapy form exists for the causal treatment of Alzheimer's dementia.

The patient affected by Alzheimer's dementia, but particularly also the relatives directly living together with this patient, see this illness as a severe burden because of its inexorably progressive character and because death is undeniably at its end.

Many strategies have therefore been proposed to slow the progression of Alzheimer's dementia, i.e. to improve the mental (cognitive) capabilities.

The medicinal strategies include the administration of:
psychostimulants such as dihydroergotoxin,
vasodilators such as papaverine, isoxuprine, cyclandelate,
stimulants such as methylphenidate, pentylenetetrazole,
substances for improving the cerebral blood circulation such as naftidofuryl, pentoxifylline, suloctidil, vincamine,
calcium channel blockers such as nimodipine,
nootropic substances such as piracetam, oxiracetam, rolziracetam, pramiracetam, aniracetam, Cl-844, Cl-933,
cholinergic active compounds such as arecoline, physostigmine, RS-86, bethanecol, BM-5,
analogs of ACTH such as ORG 2766,
vasopressins, such as DDAVP, DGAVP
somatostatin, such as L-363,586
serotonin active compounds such as alaproclate, zimelidine,
adrenergic substances such as clonidine,
hormones such as estradiol
but also of vitamins, lecithin, nicotine, tacrine and others.

It is the object of the present invention to make available a device and a procedure by means of which the symptoms of patients having Alzheimer's dementia are reduced. In particular the cognitive capabilities of these patients should be improved or the progressive character of the decrease in the mental faculties should be slowed. The object of the invention thus consists not in treatment in the classical sense with the objective of cure, but a palliative treatment of the symptoms in order to make possible to the patient a largely independent conduct of life and thus to make the care of the patient easier for the relatives and the nursing staff.

The object is achieved by a device which is capable of delivering the active compound deoxypeganine and/or a pharmaceutically acceptable acid addition salt of deoxypeganine to the patient.

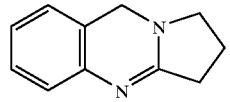

Deoxypeganine is an alkaloid of the empirical formula $C_{11}H_{12}N_2$ having the above structure, which is contained in plants of the Zygophyllaceae family. It is commercially obtainable as an acid addition salt (hydrochloride $C_{11}H_{12}N_2 \cdot HCl \cdot H_2O$).

Deoxypeganine has in fact been investigated in detail in the former Soviet Union and its pharmacological actions intensively researched, but the use according to the invention of a deoxypeganine-containing formulation for the treatment of patients having Alzheimer's dementia has not been described until now.

On account of its pharmacological properties, deoxypeganine belongs to the group of reversibly acting cholinesterase inhibitors, is related in its actions to physostigmine, neostigmine and galanthamine, but is characterized by particular specific properties. Deoxypeganine in fact inhibits not only acetylcholinesterase and thus the degradation of acetylcholine, but also monoamine oxidase and thus the degradation of dopamine. This advantage offsets its somewhat lower cholinesterase inhibitory action, related to the unit of weight (in comparison to physostigmine).

In contrast to neostigmine, deoxypeganine crosses the blood-brain barrier and antagonizes the cerebral actions of cholinergic toxins.

Deoxypeganine is obtained by isolation from the harmel peganum (Peganum harmala) or by synthesis.

In the present invention, pharmaceutical forms are employed which release the active compound preferably in a controlled (delayed) manner. Particularly preferred pharmaceutical forms are those which deliver the active compound over a relatively long period of time, e.g. approximately 12, 16, 24, 48 or 72 hours. Implanted devices which can deliver the active compound over a period of time of several days, weeks or even months are also employable according to the invention. Generally, pharmaceutical forms of this type are known in the prior art.

The administration of pharmaceutically active compounds by means of such formulations can be carried out orally, transdermally or otherwise parenterally (e.g. intracerebroventricularly, intravenously, rectally), but should preferably be carried over a prolonged period.

The medicament according to the invention for the treatment of Alzheimer's dementia comprises deoxypeganine and/or a pharmaceutically acceptable acid addition salt in an efficacious amount.

In medicaments of this type, the deoxypeganine can be present as such or in the form of pharmaceutically acceptable acid addition salts, e.g. as a hydrohalide, in particular hydrochloride or hydrobromide, or as a salt of another pharmaceutically acceptable acid, e.g. as a citrate, tartrate or acetate.

As a rule, these pharmaceutical forms furthermore contain excipients, such as vehicles, flow improvers, solvents and oils, whose nature and amounts vary depending on the administration form.

In general, the content of active compound in the medicaments, calculated as free deoxypeganine, is between 0.1 and 50% by weight, preferably between 2 and 15% by weight.

The procedure according to the invention for the treatment of Alzheimer's dementia comprises administering to a patient who is suffering from the symptoms of Alzheimer's dementia a medicament comprising deoxypeganine and/or a pharmaceutically acceptable acid addition salt of deoxypeganine. In a further embodiment of this procedure, a medicament of this type is employed in combination with a medicament known in the prior art for the treatment of Alzheimer's dementia.

What is claimed is:

1. A method for treating Alzheimer's dementia, which comprises administrating to a patient, who is suffering from Alzheimer's dementia, an effective amount of a medicament comprising deoxypeganine and/or pharmaceutically acceptable acid addition salt thereof.

2. The method according to claim 1, wherein the medicament is a controlled release pharmaceutical dosage form.

* * * * *